(12) United States Patent
Yamashita et al.

(10) Patent No.: US 8,823,376 B2
(45) Date of Patent: Sep. 2, 2014

(54) MAGNETIC RESONANCE IMAGING APPARATUS AND MAGNETIC RESONANCE IMAGING METHOD

(71) Applicants: Kabushiki Kaisha Toshiba, Minato-ku (JP); Toshiba Medical Systems Corporation, Otawara (JP)

(72) Inventors: Yuichi Yamashita, Otawara (JP); Nobuyasu Ichinose, Otawara (JP); Shinichi Kitane, Nasushiobara (JP)

(73) Assignees: Kabushiki Kaisha Tobshiba, Minato-ku (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 13/683,587

(22) Filed: Nov. 21, 2012

(65) Prior Publication Data
US 2013/0169274 A1 Jul. 4, 2013

Related U.S. Application Data

(62) Division of application No. 12/722,875, filed on Mar. 12, 2010, now Pat. No. 8,427,149.

(30) Foreign Application Priority Data

Sep. 30, 2009 (JP) .................................. 2009-228772
Jan. 21, 2010 (JP) .................................. 2010-010976

(51) Int. Cl.
*G01V 3/00* (2006.01)
*A61B 5/055* (2006.01)
(52) U.S. Cl.
USPC ........... 324/309; 324/306; 324/307; 324/318; 600/419; 382/128

(58) Field of Classification Search
USPC ........................... 324/300–322; 600/407–464; 382/128–131
See application file for complete search history.

(56) References Cited

U.S. PATENT DOCUMENTS

| | | | |
|---|---|---|---|
| 7,705,593 B1* | 4/2010 | Zhu et al. ...................... | 324/306 |
| 2003/0193334 A1 | 10/2003 | Alsop | |
| 2007/0132452 A1* | 6/2007 | Alsop ........................... | 324/306 |
| 2008/0061780 A1* | 3/2008 | Yamada et al. ............... | 324/309 |
| 2008/0071166 A1* | 3/2008 | Miyazaki ..................... | 600/419 |
| 2009/0005670 A1 | 1/2009 | Ichinose et al. | |
| 2010/0060278 A1* | 3/2010 | Park .............................. | 324/309 |
| 2011/0130668 A1* | 6/2011 | Ohyu et al. ................... | 600/504 |
| 2013/0289387 A1* | 10/2013 | Shiodera et al. .............. | 600/419 |

FOREIGN PATENT DOCUMENTS

JP 2009-028525 2/2009

* cited by examiner

*Primary Examiner* — Melissa Koval
*Assistant Examiner* — Emily Chan
(74) *Attorney, Agent, or Firm* — Nixon & Vanderhye, P.C.

(57) ABSTRACT

A magnetic resonance imaging apparatus includes a magnetic resonance data acquisition unit and a cerebrospinal fluid image data generation unit. The magnetic resonance data acquisition unit consecutively acquires a plurality of magnetic resonance data for generating a plurality of cerebrospinal fluid image data, each corresponding to a different data acquisition time, after a labeling pulse is applied. The cerebrospinal fluid image data generation unit generates the plurality of cerebrospinal fluid image data based on the plurality of magnetic resonance data.

14 Claims, 13 Drawing Sheets

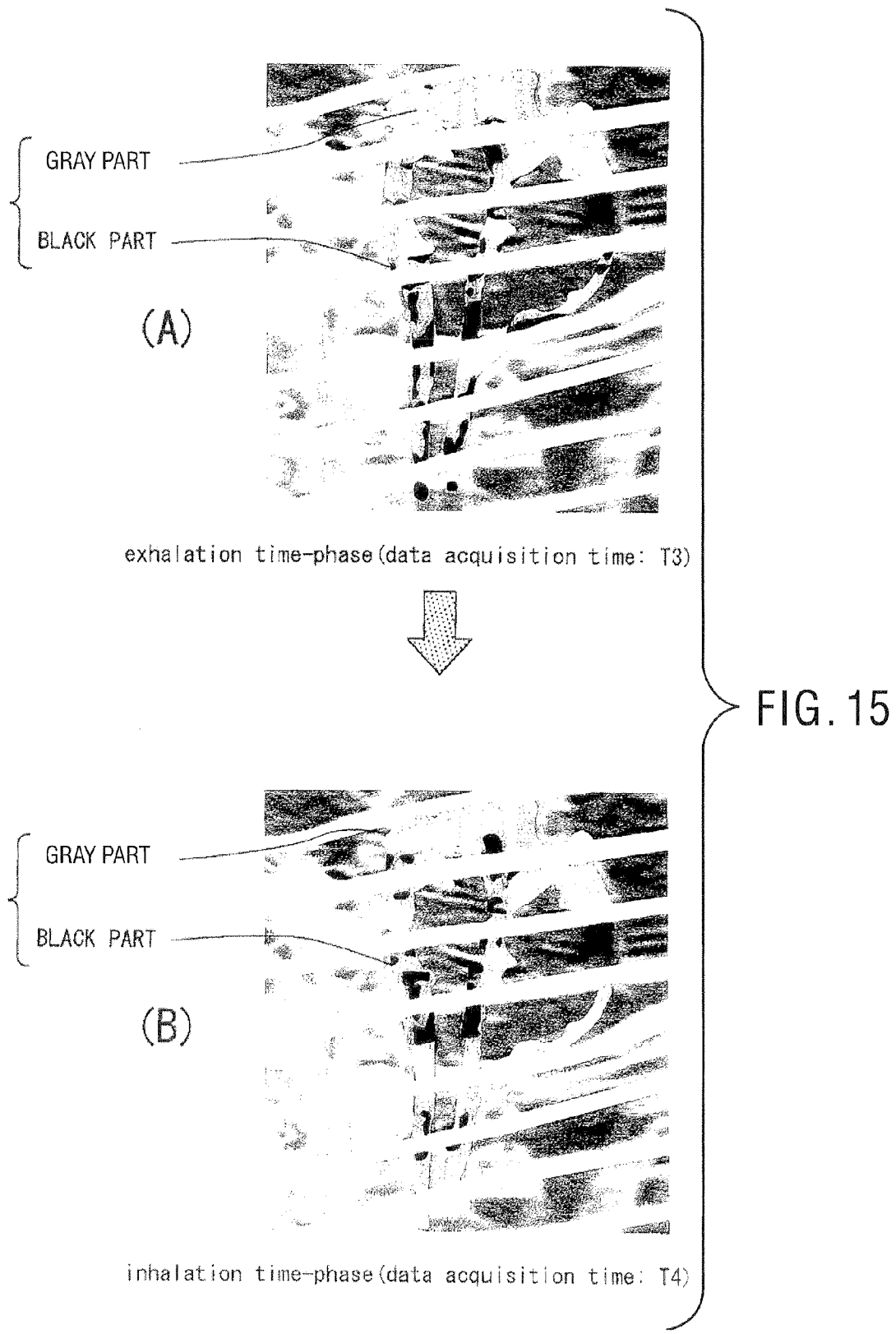

MAGNETIC RESONANCE IMAGING APPARATUS AND MAGNETIC RESONANCE IMAGING METHOD

This application is a division of application Serial No. 12/722,875 filed Mar. 12, 2010 (now U.S. Pat. No. 8,427,149 issued Apr. 23, 2013), which claims priority based on Japanese Patent Application Nos. 2009-228772 filed Sep. 30, 2009, and 2010-010976 filed Jan. 21, 2010, the entire contents of all of which are hereby incorporated by reference.

BACKGROUND

1. Technical Field

The present exemplary embodiments relate to MRI (magnetic resonance imaging) which magnetically excites nuclear spin of an object with an RF (radio frequency) signal having the Larmor frequency and reconstructs an image based on NMR (nuclear magnetic resonance) signals generated due to the excitation. More particularly, the present exemplary embodiments relate to a magnetic resonance imaging apparatus and a magnetic resonance imaging method that can image CSF (cerebrospinal fluid).

2. Related Art

Magnetic Resonance Imaging (MRI) is an imaging method that excites nuclear spin of an object set in a static magnetic field with an RF signal having the Larmor frequency magnetically and reconstructs an image based on NMR signals generated due to the excitation.

In the field of the magnetic resonance imaging, MRA (magnetic resonance angiography) is known as a method of obtaining an image of a blood flow. An MRI without using a contrast medium is referred to as a non-contrast MRA. As the non-contrast enhanced MRA, an FBI (fresh blood imaging) method that performs an ECG (electrocardiogram) synchronization to capture a pumping blood flow is ejected from the heart, thereby satisfactorily representing a blood vessel.

In MRA, "labeling" (synonymous with tagging) is performed on blood in order to better depict a blood vessel. As a method of labeling blood, there is known a time spatial labeling inversion pulse (t-SLIP) method (for example, see Japanese Patent Laid-Open No. 2009-28525). According to the t-SLIP method, a specific blood vessel can be selectively depicted using a non-contrast MRA.

FIG. 1 is an explanatory drawing explaining a data acquisition method using a conventional t-SLIP method.

In FIG. 1, the abscissa axis indicates time. As illustrated in FIG. 1, according to the t-SLIP method, when a region selective inversion recovery (IR) pulse is applied as a labeling pulse, the blood in a labeling region is labeled. Then, when a BBTI (Black Blood Traveling Time) has elapsed since the region selective IR pulse is applied, imaging data acquisition is performed. Then, as illustrated in FIG. 1, in order to make dynamic observation on a blood flow, the BBTI is changed for each data acquisition before imaging is performed. For this reason, if a large number of different BBTIs with small difference are set, dynamic observation can be made on the blood flow corresponding to a more detailed change in time.

Further, in the t-SLIP method, a method of applying a plurality of labeling pulses has been devised.

FIG. 2 is a drawing explaining a data acquisition method with application of a plurality of labeling pulses using the conventional t-SLIP method.

In FIG. 2, the abscissa axis indicates time. As illustrated in FIG. 2, according to the t-SLIP method, a plurality of BBTIs can be set to one data acquisition by applying a plurality of labeling pulses at each different timing. In addition, the spatial position of applied labeling pulses can also be changed. By doing so, not only various blood vessels but also the CSF can be selectively depicted or suppressed.

However, the CSF has no periodicity such as a cardiac cycle and the CSF flow greatly changes for each data acquisition timing. In light of this, from images acquired by the t-SLIP method, it is possible to understand a dynamic behavior of a periodic fluid, but it is difficult to understand a dynamic behavior of a non-periodic fluid accurately.

Moreover, when a plurality of labeling pulses are applied, the periods from the application timing of the respective labeling pulse to data acquisition timing are changed respectively. For this reason, the method of applying a plurality of labeling pulses cannot generate images representing a dynamic fluid behavior of synchronous time.

Furthermore, the CSF is greatly different in flow depending on its position. In light of this, the t-SLIP method of performing data acquisition a plurality of times by changing the BBTI has difficulty in following and imaging the CSF whose flow is changed. Moreover, in order to understand the CSF flow at a plurality of positions using the t-SLIP method, imaging needs to be performed at a different timing for each position. For this reason, the t-SLIP method cannot allow a wide range of CSF flow of synchronous time to be understood.

In addition, in the t-SLIP method, contrast is greatly changed due to a change in the period from the application timing of the labeling pulse to the data acquisition timing. For this reason, in the t-SLIP method, it is very difficult to visually understand a detailed dynamic CSF behavior from monochrome image in grayscale.

BRIEF SUMMARY

The present exemplary embodiments aim to provide a technology capable of imaging an image allowing a dynamic behavior of CSF to be better understood without using a contrast medium in magnetic resonance imaging.

In order to achieve the aforementioned aim, the present exemplary embodiments provide a magnetic resonance imaging apparatus comprising a magnetic resonance data acquisition unit and a cerebrospinal fluid image data generation unit.

The magnetic resonance data acquisition unit consecutively acquires a plurality of magnetic resonance data for generating a plurality of cerebrospinal fluid image data, each corresponding to a different acquisition time, after a labeling pulse is applied.

The cerebrospinal fluid image data generation unit generates the plurality of cerebrospinal fluid image data based on the plurality of magnetic resonance data so as to correspond to each of the plurality of magnetic resonance data.

In order to achieve the aforementioned aim, the present exemplary embodiments also provide a magnetic resonance imaging method comprising the steps of: applying a labeling pulse;

acquiring a plurality of magnetic resonance data for generating a plurality of cerebrospinal fluid image data, each corresponding to a different acquisition time, after the labeling pulse is applied; and generating the plurality of cerebrospinal fluid image data based on the plurality of magnetic resonance data.

According to the aforementioned magnetic resonance imaging of the present exemplary embodiments, it is possible to acquire a CSF image allowing a dynamic behavior of CSF to be better understood without using a contrast medium.

BRIEF DESCRIPTION OF THE DRAWINGS

In the accompanying drawings:

FIG. 15 is a chart showing an example of a plurality of CSF images, each corresponding to a different time, displayed in chronological order in the same manner as in FIG. 14, when monitoring is performed on the abdominal motion.

DESCRIPTION OF EXEMPLARY EMBODIMENTS

A magnetic resonance imaging apparatus and a magnetic resonance imaging method according to exemplary embodiments of the present invention will be described with reference to the accompanying drawings.

(Configuration and Function)

Figure 3:
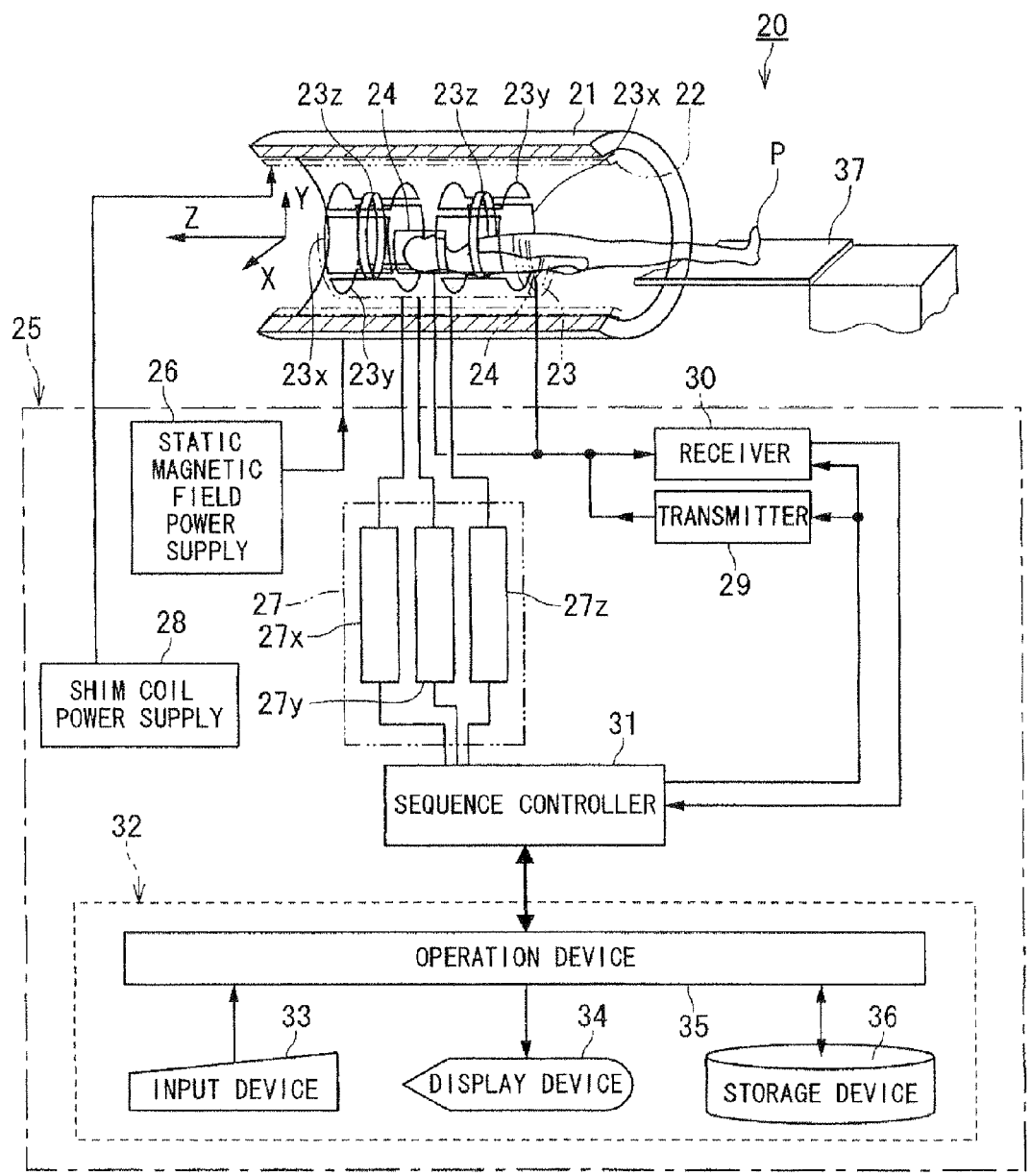
FIG. 3 is a block diagram showing a magnetic resonance imaging apparatus according to an exemplary embodiment of the present invention.

FIG. 3 is a block diagram showing a magnetic resonance imaging apparatus according to an embodiment of the present invention.

A magnetic resonance imaging apparatus 20 includes a cylinder-shaped static field magnet 21 for generating a static magnetic field, a cylinder-shaped shim coil 22 arranged inside the static field magnet 21, a gradient coil 23 and RF coils 24.

The magnetic resonance imaging apparatus 20 also includes a control system 25. The control system 25 includes a static magnetic field power supply 26, a gradient magnetic field power supply 27, a shim coil power supply 28, a transmitter 29, a receiver 30, a sequence controller 31 and a computer 32. The gradient magnetic field power supply 27 of the control system 25 includes an X-axis gradient magnetic field power supply 27x, a Y-axis gradient magnetic field power supply 27y and a Z-axis gradient magnetic field power supply 27z. The computer 32 includes an input device 33, a display device 34, an operation device 35 and a storage device 36.

The static field magnet 21 is electrically connected to the static magnetic field power supply 26 and has a function to generate a static magnetic field in an imaging region by using electric current supplied from the static magnetic field power supply 26. The static field magnet 21 includes a superconductivity coil in many cases. The static field magnet 21 gets electric current from the static magnetic field power supply 26 which is electrically connected to the static field magnet 21 at excitation. However, once excitation has been made, the static field magnet 21 is usually isolated from the static magnetic field power supply 26. The static field magnet 21 may include a permanent magnet, which makes the static magnetic field power supply 26 unnecessary.

The cylinder-shaped shim coil 22 is coaxially arranged inside the static field magnet 21. The shim coil 22 is electrically connected to the shim coil power supply 28. The shim coil power supply 28 supplies electric current to the shim coil 22 so that the static magnetic field becomes uniform.

The gradient coil 23 includes an X-axis gradient coil 23x, a Y-axis gradient coil 23y and a Z-axis gradient coil 23z. Each of the X-axis gradient coil 23x, the Y-axis gradient coil 23y and the Z-axis gradient coil 23z is cylinder-shaped and arranged inside the static field magnet 21. A bed 37 is arranged inside the gradient coil 23 and the area inside the gradient coil 23 is an imaging area. The bed 37 supports an object (for example, a patient) P. The RF coils 24 include a WBC (whole body coil) built in the gantry for transmission and reception of RF signals and local coils arranged around the bed 37 or the object P for reception of RF signals.

The gradient coil 23 is electrically connected to the gradient magnetic field power supply 27. The X-axis gradient coil 23x, the Y-axis gradient coil 23y and the Z-axis gradient coil 23z of the gradient coil 23 are electrically connected to the X-axis gradient magnetic field power supply 27x, the Y-axis gradient magnetic field power supply 27y and the Z-axis gradient magnetic field power supply 27z of the gradient magnetic field power supply 27 respectively.

The X-axis gradient magnetic field power supply 27x, the Y-axis gradient magnetic field power supply 27y and the Z-axis gradient magnetic field power supply 27z supply electric currents to the X-axis gradient coil 23x, the Y-axis gradient coil 23y and the Z-axis gradient coil 23z respectively so as to generate gradient magnetic field Gx in the X-axis direction, gradient magnetic field Gy in the Y-axis direction and gradient magnetic field Gz in the Z-axis direction in the imaging area.

The RF coils 24 are electrically connected to the transmitter 29 and/or the receiver 30. The transmission RF coil 24 has a function to transmit a RF signal given from the transmitter 29 to the object P. The reception RF coil 24 has a function to receive an NMR signal generated due to excited nuclear spin inside the object P by the RF signal and give the received NMR signal to the receiver 30.

The sequence controller 31 of the control system 25 is electrically connected to the gradient magnetic field power supply 27, the transmitter 29 and the receiver 30. The sequence controller 31 has a function to storage sequence information describing control information needed in order to make the gradient magnetic field power supply 27, the transmitter 29 and the receiver 30 drive. The aforementioned control information includes motion control information, such as intensity, impression period and impression timing of the pulse electric current which should be impressed to the gradient magnetic field power supply 27. The sequence controller 31 also has a function to generate gradient magnetic fields Gx, Gy and Gz in the X-axis, Y-axis and Z-axis directions and RF signals by driving the gradient magnetic field power supply 27, the transmitter 29 and the receiver 30 according to a predetermined sequence stored.

The sequence controller 31 is also configured to receive raw data, which are complex data obtained through the detection of an NMR signal and A/D conversion to the NMR signal detected in the receiver 30, and input the raw data to the computer 32.

Therefore, the transmitter 29 has a function to give an RF signal to the RF coil 24 in accordance with the control information provided from the sequence controller 31. The receiver 30 has a function to generate raw data that are digitized complex number data obtained by detecting an NMR signal given from the RF coil 24, performing predetermined signal processing to the NMR signal detected, and performing A/D conversion to the NMR signal after the predetermined signal processing. The receiver 30 also has a function to give the generated raw data to the sequence controller 31.

The computer 32 gets various functions by the operation device 35 executing some programs stored in the storage device 36 of the computer 32. Alternatively, some specific circuits having various functions may be provided with the magnetic resonance imaging apparatus 20 instead of using some of the programs.

Figure 4:
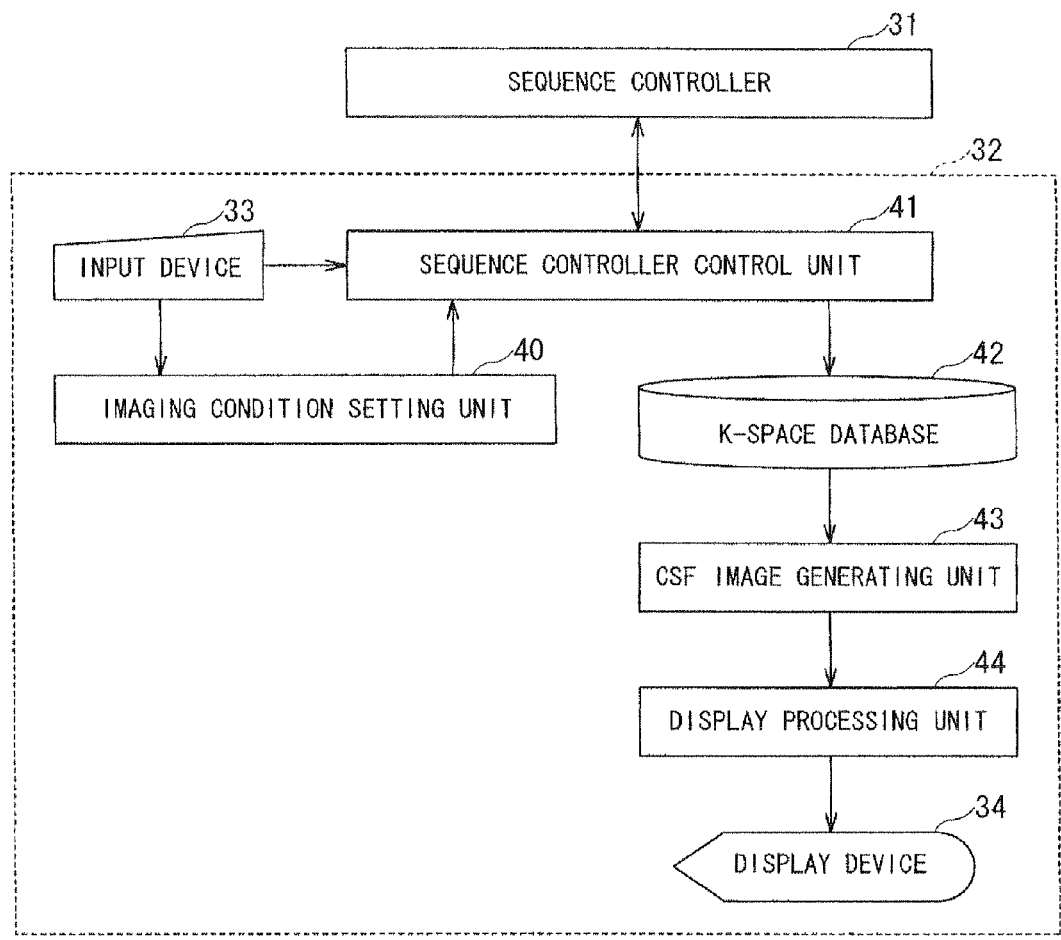
FIG. 4 is a functional block diagram of the computer 32 shown in FIG. 3.

FIG. 4 is a functional block diagram of the computer 32 shown in FIG. 3.

The computer 32 functions as an imaging condition setting unit 40, a sequence controller control unit 41, a k-space database 42, a CSF image generating unit 43 and a display processing unit 44.

The imaging condition setting unit 40 has a function to set an imaging condition including a pulse sequence based on instruction from the input device 33 and to provide the set imaging condition to the sequence controller control unit 41. Especially, the imaging condition setting unit 40 has a function to set a pulse sequence to acquire a CSF image without using a contrast medium. More concretely, the imaging condition setting unit 40 has a function to set a sequence for selectively depicting a non-periodic CSF by labeling.

Labeling for identifying (distinguishing) a CSF can be performed by applying a labeling pulse to the CSF or a region of interest. As the pulses available as the labeling pulse, a t-SLIP, a saturation (SAT) pulse, a SPAMM (spatial modulation of magnetization) pulse, and a DANTE (delays alternating with nutations for tailored excitation) pulse are known.

The t-SLIP includes a region non-selective IR pulse and a region selective IR pulse. Note that the region non-selective IR pulse can be switched on/off. The labeling region where a region selective IR pulse is applied can be arbitrarily set independently of an imaging region. Note that the imaging condition may be set so as to apply a plurality of t-SLIPs.

A region selective 90° SAT pulse is obtained by bending a magnetization vector in a selected slab region by 90° to saturate longitudinal magnetization. Note that the imaging condition may be set so as to apply not only a single but also a plurality of region selective 90° SAT pulses. When the plurality of region selective 90° SAT pulses are applied and a plurality of selective slab regions can be set to a radial or stripe-shaped pattern.

The SPAMM pulse is also called a rest grid pulse and was originally developed to monitor cardiac motion. The SPAMM pulse is a region-non-selectively applied pulse, and can form a region saturated with a desired pattern such as a stripe pattern, a grid pattern (lattice shaped pattern), and a radial pattern by adjusting a gradient magnetic field. The saturation pattern functions as a position marker, and thus an image showing a CSF flow can be obtained by imaging with application of the SPAMM pulse.

The DANTE pulse is also a labeling pulse for forming a region saturated with a desired pattern such as a stripe pattern, a grid pattern, and a radial pattern. The SPAMM pulse and the DANTE pulse each are a pulse equivalent to a plurality of SAT pulses applied at the same time.

Further, the imaging condition can be set so that a combination of a single t-SLIP or SAT pulse or a plurality of t-SLIPS or SAT pulses with the SPAMM pulse or the DANTE pulse can be applied as the labeling pulse.

Figure 5:
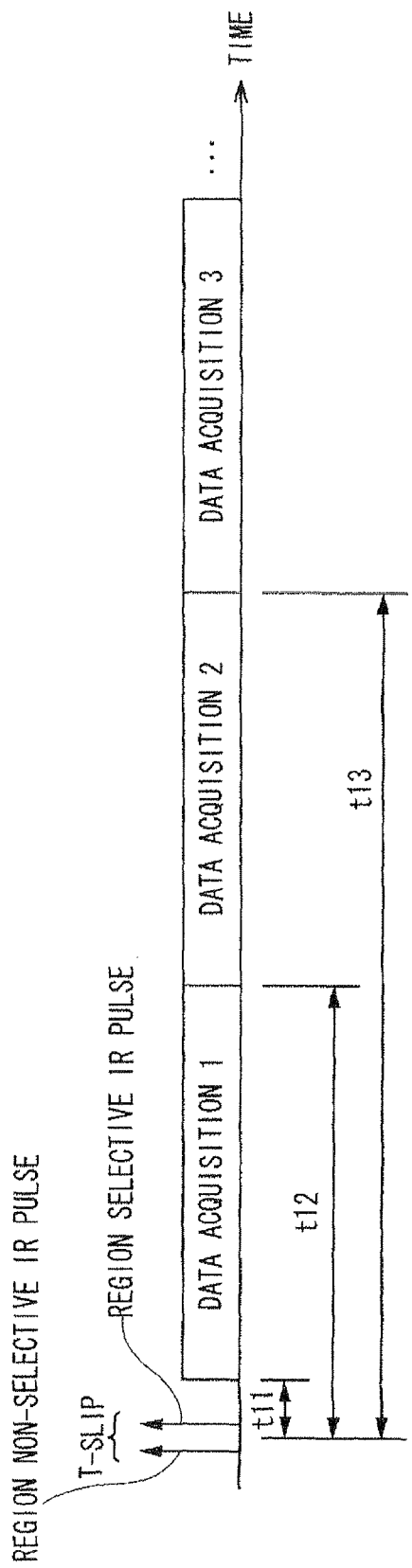
FIG. 5 is a chart illustrating imaging conditions with pulse application under the t-SLIP method set by the imaging condition setting unit 40 illustrated in FIG. 4.

FIG. 5 illustrates imaging conditions with application of the t-SLIP pulse set by the imaging condition setting unit 40 illustrated in FIG. 4.

In FIG. 5, the abscissa axis indicates time. As illustrated in FIG. 5, after the t-SLIP is applied, data acquisition is consecutively (continuously) repeated a plurality of times DATA ACQUISITION 1, DATA ACQUISITION 2, DATA ACQUISITION 3, and so on). Consequently, time-series data at a different time continuous in terms of time such as t11, t12, t13, and so on can be acquired. In other words, imaging data of a plurality of frames, each corresponding to a respective imaging time, are acquired after application of a labeling pulse.

Figure 1:
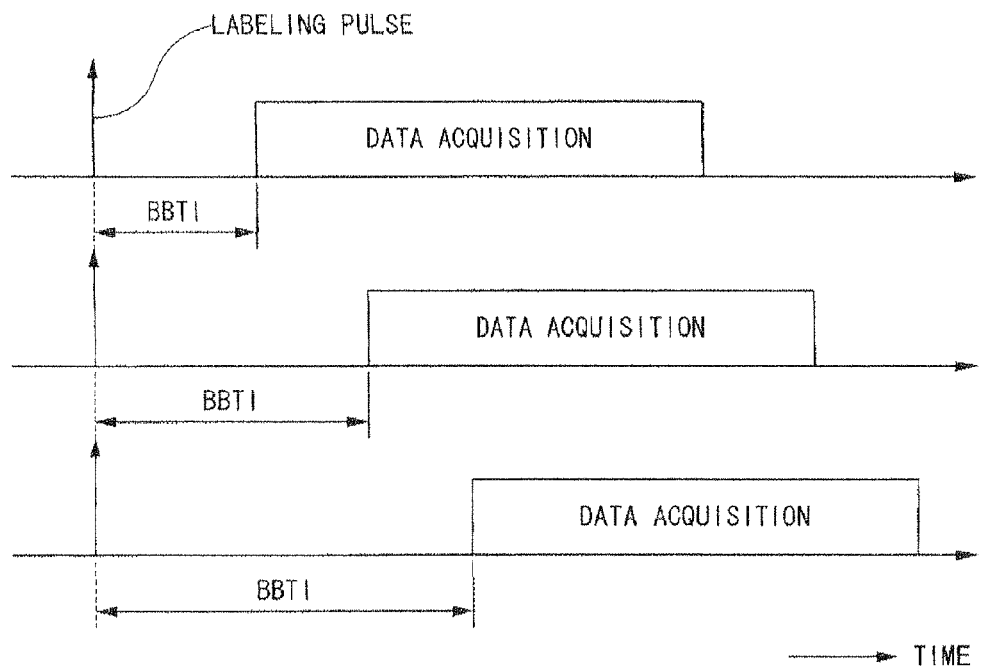
FIG. 1 is a chart explaining a data acquisition method by using a conventional t-SLIP method.
Figure 2:
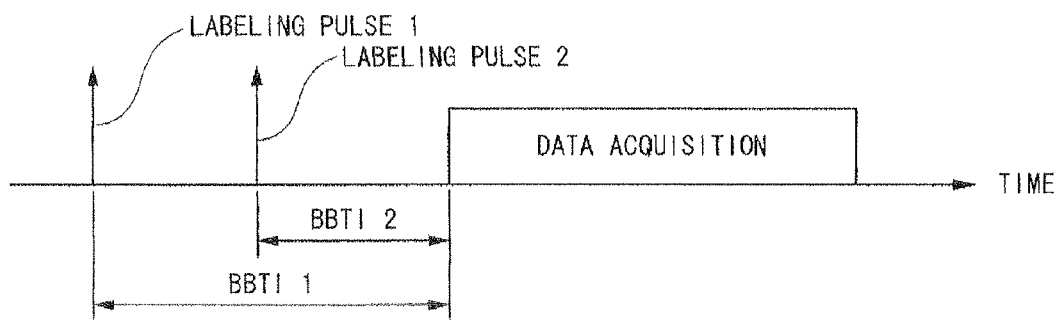
FIG. 2 is a chart explaining a data acquisition method with application of a plurality of labeling pulses by using the conventional t-SLIP method.

More specifically, according to the conventional technique, as illustrated in FIG. 1, labeling is performed and then data of one frame is acquired, and then labeling is performed again and then data of another frame is acquired, and this operation is repeated. Consequently, according to the conventional technique, the labeled CSF is different for each frame. In contrast, according to the present invention, as illustrated in FIG. 5, labeling is performed once, and then data acquisition corresponding to each frame of CSF image is consecutively performed. Thus, the labeled CSF is the same for each frame. Therefore, the CSF image acquisition method according to the present invention allows the dynamic CSF behavior to be understood more accurately and continuously in terms of time.

When a region non-selective IR pulse is turned on, the region non-selective IR pulse and a region selective IR pulse are applied at approximately the same time. The period t11 from the application timing of the t-SLIP to the acquisition timing of the first data can be appropriately set according to the imaging conditions such as a setting position of a labeling region by the region selective IR pulse, a setting position of a region of interest for depicting the CSF, a longitudinal magnetization relaxation time in a background portion.

The imaging by the t-SLIP method includes a flow-in method and a flow-out method. The flow-in method is to depict unlabeled CSF flowing into a region of interest from outside the region of interest by applying the region selective IR pulse to the region of interest to invert the longitudinal magnetization in the region of interest. In contrast, the flow-out method is to selectively depict labeled CSF flowing into a region of interest from the labeling region by applying the region non-selective IR pulse to invert the longitudinal magnetization as well as by applying the region selective IR pulse to the labeling region to invert the longitudinal magnetization of the CSF inside the labeling region to a positive value. In other words, in the flow-in method, the labeling region is set inside the region of interest; while in the flow-out method, the labeling region is set outside the region of interest.

For this reason, the data acquisition timing can be determined so that the data acquisition starts after the CSF flows into the region of interest. If the longitudinal magnetization of the background portion is inverted by the region non-selective IR pulse, the data acquisition timing may be determined so that the data acquisition starts at a timing when the absolute value of the longitudinal magnetization of the background portion becomes around zero by longitudinal relaxation.

Such a method of using the t-SLIP as the labeling pulse is effective, especially when the magnetic resonance imaging apparatus 20 can generate a high magnetic field equal to or greater than 3T and a relaxation time for determining tag duration time is long.

Figure 6:
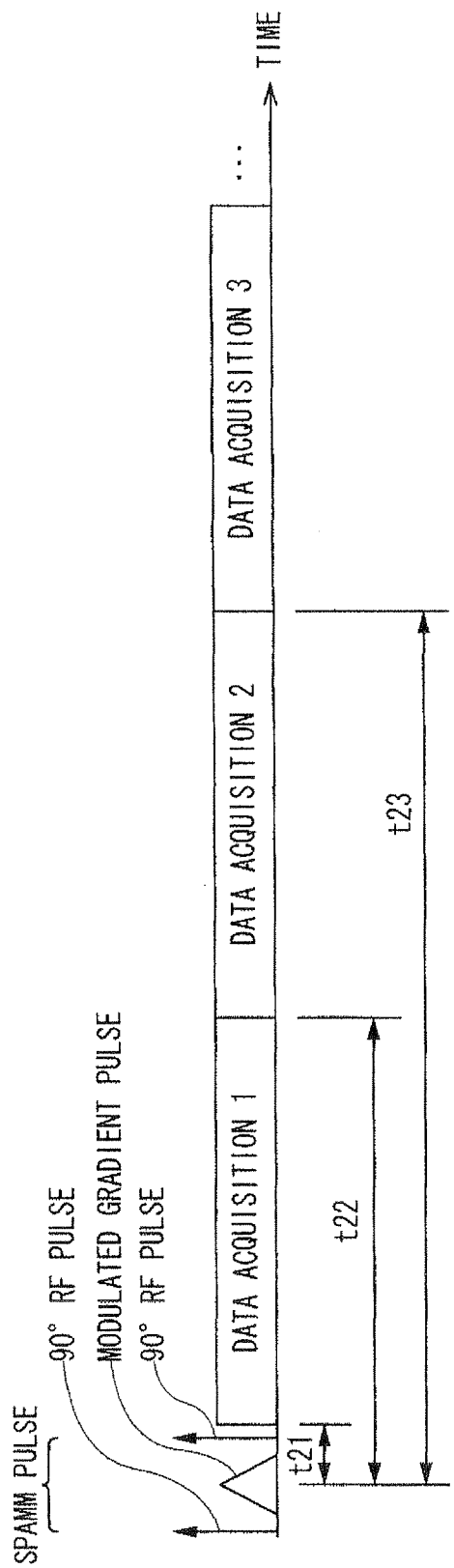
FIG. 6 is a chart illustrating imaging conditions with application of the SPAMM pulse set by the imaging condition setting unit 40 illustrated in FIG. 4.

FIG. 6 illustrates imaging conditions with application of the SPAMM pulse set by the imaging condition setting unit 40 illustrated in FIG. 4.

In FIG. 6, the abscissa axis indicates time. As illustrated in FIG. 6, after the SPAMM pulse is applied, data acquisition is consecutively (continuously) repeated a plurality of times (DATA ACQUISITION 1, DATA ACQUISITION 2, DATA ACQUISITION 3, and so on). Consequently, time-series data continuous in terms of time such as t21, t22, t23, and so on can be acquired. Thus, the same advantage as case of applying the t-SLIP can be obtained.

The SPAMM pulse includes an RF pulse and a modulated gradient pulse. FIG. 6 illustrates an example of the SPAMM pulse which is configured by providing the modulated gradient pulse between the two 90° RF pulses. The width of the stripe pattern and the grid pattern can be controlled by adjusting the waveform and the application axis of the modulated gradient pulse. A wide pattern formed by application of the SPAMM pulse moves with the CSF flow. Consequently, if the SPAMM pulse is used as the labeling pulse, it is possible to obtain a CSF image capable of observing a dynamic CSF behavior in a wide range at the same imaging time. Moreover, since the pattern moves with the CSF flow, the period t21 from the application timing of the SPAMM pulse to the acquisition timing of the first data can be shortly set, so that the period t21 becomes substantially zero.

Note that the grid pattern takes about double application time of labeling pulse of the stripe pattern. The radial pattern takes more application time of labeling pulse than the grid pattern. Therefore, it is preferable that a desired pattern such as a stripe pattern, a grid pattern, and a radial pattern is selected as the pattern of the labeling region according to the imaging purpose and imaging conditions.

Note that in FIGS. 5 and 6, any sequence such as an SSFP (steady state free precession) sequence and a FASE (Fast ASE: fast asymmetric spin echo or fast advanced spin echo) sequence can be used as a sequence for acquiring imaging data.

If the timing of applying the labeling pulse such as the t-SLIP, the SAT pulse, the SPAMM pulse, and the DANTE pulse is determined based on a trigger signal, any signal such as a biological signal, an ECG (electrocardiogram) signal, a respiratory gating signal by a respiratory sensor (respiratory gating), and a PPG (peripheral pulse gating) signal and a clock signal can be used as the trigger signal. When the ECG signal or the PPG signal is used, an ECG unit or a PPG signal detection unit is connected to the magnetic resonance imaging apparatus 20.

It is desirable to display information on "which time phase of respiration or heartbeat imaging time of each frame corresponds to" in parallel with each frame, when the respiratory gating signal and(or) the ECG signal of an object P are (is) acquired at the same time of imaging data acquisition and CSF images are displayed after this imaging. If the respiratory gating signal is used, it is preferable that the period required to acquire imaging data of one frame (period of the DATA ACQUISITION 1 in FIGS. 5 and 6) should be sufficiently short with respect to a cycle of respiration. If the cycle of respiration is about seconds, it is preferable that the period required to acquire imaging data of one frame should be, for example, equal to or less than 0.3 second.

Likewise, it is desirable to display information on "which time phase of body motion imaging time of each frame corresponds to" in parallel with each frame, when the body motion at a predetermined position such as abdominal expansion and contraction by respiration is monitored at the same time of imaging data acquisition and CSF images are displayed after this imaging. In this case, it is also preferable that the period required to acquire imaging data of one frame should be sufficiently short as compared with a cycle of body motion.

Before the labeling pulse such as the SPAMM pulse and the DANTE pulse is applied, the region non-selective IR pulse may be applied. This is because the period, in which CSF is observable, is considered to be longer as described below.

Figure 7:
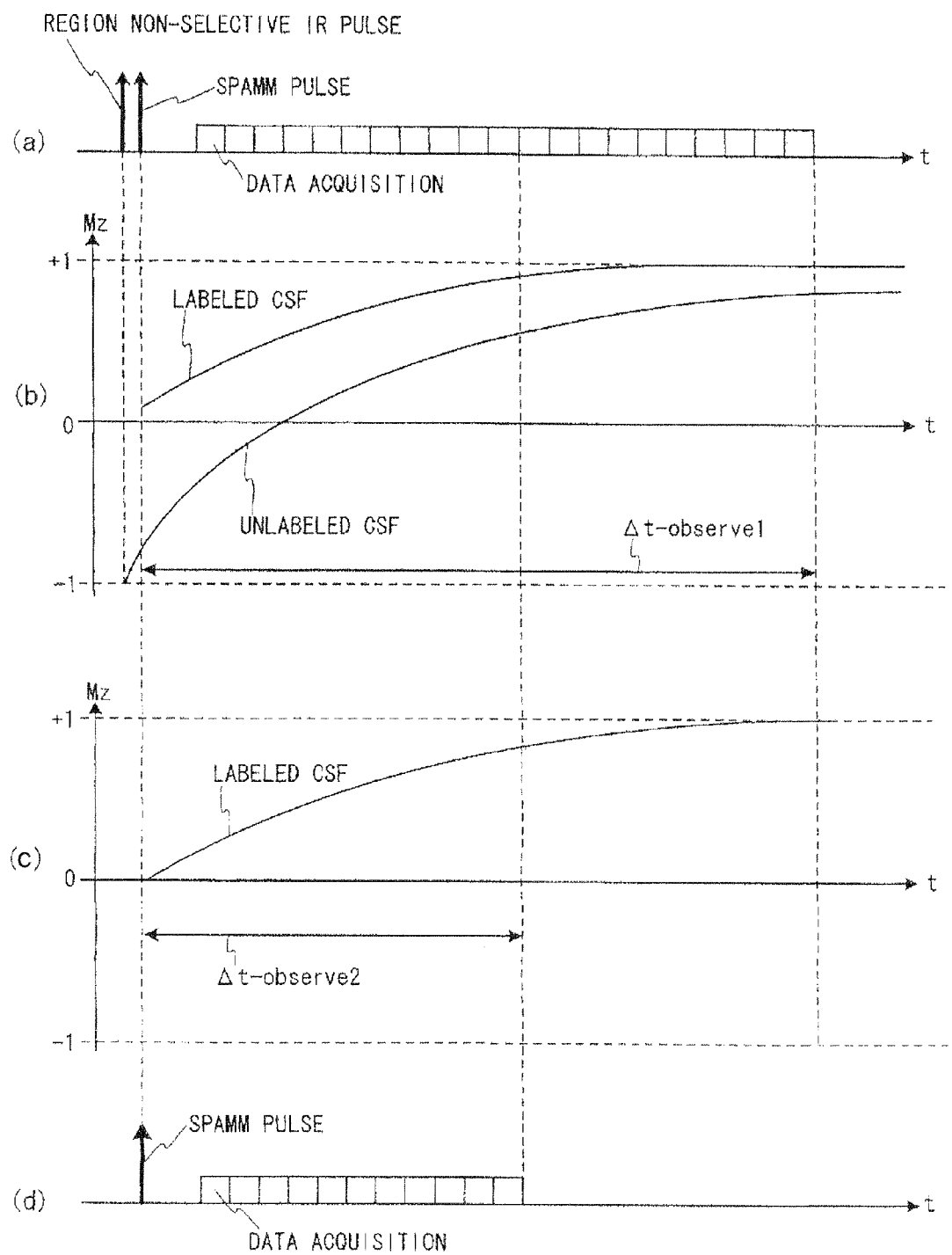
FIG. 7 is a timing chart illustrating pulse sequences with and without application of the region non-selective IR pulse before the application of the labeling pulse, together with recovery processes of the longitudinal magnetization component Mz of a spin.

FIG. 7 is a timing chart illustrating pulse sequences with and without application of the region non-selective IR pulse before the application of labeling pulse, together with recovery processes of the longitudinal magnetization component Mz of a spin. In FIGS. 7A to 7D, the abscissa axis indicates elapsed time t. In FIGS. 7B and 7C, the vertical (longitudinal) axis indicates longitudinal magnetization component Mz. Here, as an example, the SPAMM pulse as a saturation pulse is used as the labeling pulse.

FIG. 7A illustrates a pulse sequence when the region non-selective IR pulse is applied before the application of the labeling pulse. FIG. 7B illustrates a recovery process of the longitudinal magnetization component Mz following the pulse sequence illustrated in FIG. 7A. For ease of comparison between the differences in recovery process of the longitudinal magnetization component Mz, FIG. 7C is provided under FIG. 7B, which illustrates a recovery process of the longitudinal magnetization component Mz when the region non-selective IR pulse is not applied. FIG. 7D illustrates a pulse sequence when the region non-selective IR pulse is not applied before the application of the labeling pulse. The recovery process of the longitudinal magnetization component Mz illustrated in FIG. 7C follows the pulse sequence illustrated in FIG. 7D.

When the region non-selective IR pulse is not applied, as illustrated in FIG. 7C, the longitudinal magnetization component Mz of the CSF labeled by the SPAMM pulse is gradually returned to the magnetostatic field direction from a state of being bent 90°. Here, when the difference in signal level of the NMR signal between labeled CSF and unlabeled CSF is a predetermined value or more, namely, when the difference in longitudinal magnetization component Mz between the aforementioned two types of CSF is a predetermined value or more, the two types of CSF are considered to be distinguishable (observable). Thus, when the region non-selective IR pulse is not applied, the data acquisition period, in which CSF is observable, is as indicated by Δt-observe 2 in FIG. 7C.

In contrast, when the region non-selective IR pulse is applied, the longitudinal magnetization component Mz of the unlabeled CSF is inverted by 180° after the application of the region non-selective IR, and then recovers to the static magnetic field direction, with the elapse of time, as illustrated in FIG. 7B. Then, as illustrated in FIG. 7B, the CSF labeled by the SPAMM pulse after the application of the region non-selective IR pulse recovers the longitudinal magnetization component Mz of the spin to the magnetostatic field direction by 90°. For this reason, the longitudinal magnetization component Mz of the labeled CSF is recovered to the magnetostatic field direction earlier than that of the unlabeled CSF. Subsequently, with the recovery of the longitudinal magnetization component Mz of the unlabeled CSF, the CSF can be observed until the difference in longitudinal magnetization component Mz between the labeled CSF and the unlabeled CSF reach a predetermined value. In this case, the data acquisition period, in which CSF is observable, is as indicated by Δt-observe 1 in FIG. 7B, which is longer than Δt-observe 2 in FIG. 7C. Therefore, when the region non-selective IR pulse is applied before the application of the labeling pulse, the period in which CSF is observable becomes longer.

When the region non-selective IR pulse is applied before the application of the labeling pulse as described above, in the process of processing the NMR signal and generating image data, it is preferable to perform REAL reconstruction processing using the real part (not absolute value) of a magnetic resonance signal which is a complex signal.

More specifically, when the region non-selective IR pulse is applied before, the longitudinal magnetization component Mz of the NMR signal is a negative value in the initial stage of data acquisition. In contrast to this, when a general image reconstruction is performed, for example, the square root of the sum of 'the square of the real part' and 'the square of the imaginary part' becomes a luminance level as the absolute value. In this case, both the NMR signals corresponding to its longitudinal magnetization component being −1 and 1 become equal in terms of luminance, and the luminance of each NMR signal is displayed in the range of 0 to 1.

Meanwhile, when the NMR signal whose longitudinal magnetization component is a negative value (e.g., −1) is processed as the negative value by the REAL reconstruction processing and a predetermined signal level (corresponding to a longitudinal magnetization component of 1) is added to the NMR signal, the luminance level of the NMR signal can be displayed in the range of 0 to 2. In other words, the dynamic range can be larger than the case without the REAL reconstruction processing.

Next, the other functions of the computer 32 will be described.

The sequence controller control unit 41 has a function to instruct the sequence controller 31 to perform drive control by providing imaging conditions including a pulse sequence based on information from the input device 33. In addition, the sequence controller control unit 41 has a function to receive raw data from the sequence controller 31 and to store the data as k-space data in a k-space formed in the k-space database 42.

The CSF image generating unit 43 has a function to obtain the k-space data from the k-space database 42, and to generate time series CSF image data by performing data processing including image reconstruction processing.

The display processing unit 44 has a function to perform display processing such as coloring of the CSF portion on the CSF image data and has a function to display the CSF image on the display device 34 after the display processing.

(Operation and Behavior)

Next, the operation and the behavior of the magnetic resonance imaging apparatus 20 will be described.

Figure 8:
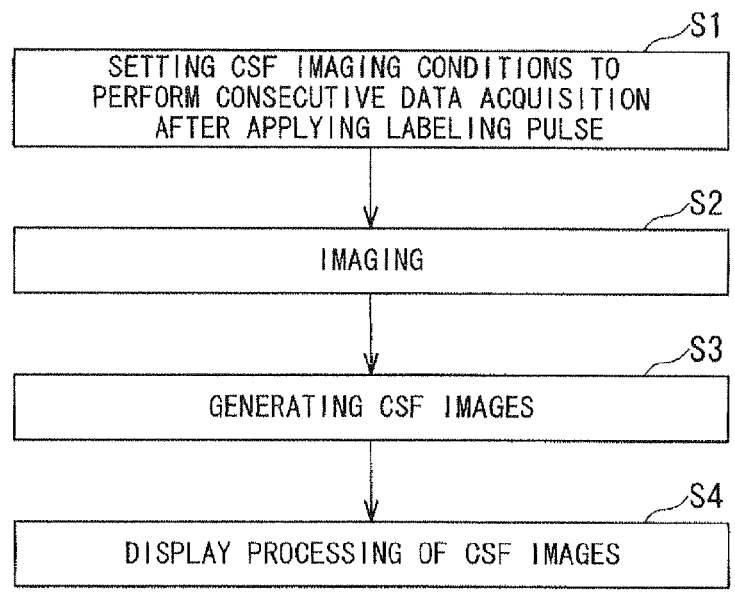
FIG. 8 is a flowchart illustrating a flow of imaging a non-contrast CSF image of an object P by using the magnetic resonance imaging apparatus of the present invention.

FIG. 8 is a flowchart illustrating a flow of imaging a non-contrast CSF image of an object P by using the magnetic resonance imaging apparatus 20 illustrated in FIG. 3.

First, in step S1, the imaging condition setting unit 40 sets the CSF imaging conditions for performing consecutive data acquisition after the labeling pulse is applied, as illustrated in FIGS. 5, 6 and 7A or 7D (in the case of FIG. 7A, also set the imaging condition of the region non-selective IR pulse applied before the labeling pulse). As the labeling pulse, the t-SLIP, the SAT pulse, the SPAMM pulse or the DANTE pulse may be used.

Then, in step S2, imaging scan is performed on the CSF according to the set imaging conditions.

The object P is set on the bed 37 in advance. Then, a static magnetic field is formed in an imaging region inside the static magnetic field magnet 21 (superconducting magnet) excited by the static magnetic field power supply 26. In addition, electric current is supplied from the shim coil power supply 28 to the shim coil 22, and thereby the static magnetic field formed in the imaging region is made uniform.

Then, when the sequence controller control unit 41 receives a scan start instruction from the input device 33, the sequence controller control unit inputs the imaging conditions including the pulse sequence acquired from the imaging condition setting unit 40 to the sequence controller 31. The sequence controller 31 drives the gradient magnetic field power supply 27, the transmitter 29, and the receiver 30 according to the inputted pulse sequence, thereby a gradient magnetic field is formed in the imaging region, where the object P is set, and an RF signal is generated from the RF coil 24.

Then, an NMR signal generated by nuclear magnetic resonance (NMR) inside the object P is detected by the RF coil 24 and inputted to the receiver 30. The receiver 30 receives the NMR signal from the RF coil 24, performs required signal processing and then A/D conversion on the received NMR signal to generate raw data, which is digital data of the NMR signal. The receiver 30 inputs the generated raw data to the sequence controller 31. The sequence controller 31 inputs the raw data to the sequence controller control unit 41. The sequence controller control unit 41 stores the raw data in the k-space formed in the k-space database 42 as k-space data.

Note that in parallel with the aforementioned pulse sequence and reception of the NMR signal from the object P (data acquisition operation), acquisition of a respiratory gating signal or an ECG signal from the object P or monitoring of the body motion of a predetermined portion of the object P may be performed.

Then, in step S3, the CSF image generating unit 43 obtains the k-space data from the k-space database 42, performs data processing including the image reconstruction processing on the k-space data, and generates the time-series CSF image data. Note that if, in step S2, the region non-selective IR pulse is applied before the application of the labeling pulse, the REAL reconstruction processing is used as part of the image reconstruction processing in step S3.

Figure 9:
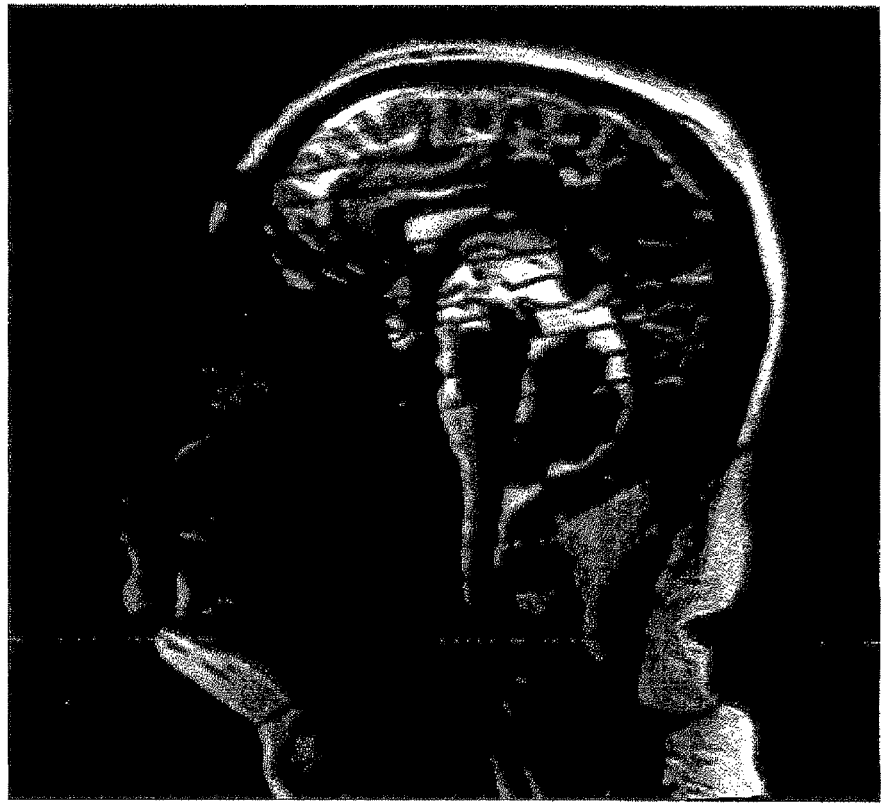
FIG. 9 is a chart showing an example of a CSF image imaged by the magnetic resonance imaging apparatus of the present invention.

FIG. 9 illustrates an example of the CSF image imaged by the magnetic resonance imaging apparatus 20 illustrated in FIG. 3.

FIG. 9 illustrates the CSF image at a time of being acquired with application of the DANTE pulse. It can be confirmed that a stripe pattern is generated by the DANTE pulse. It can also be confirmed that the stripe pattern also moves with the CSF flow. It is possible to perform display processing on the CSF image data so as to better observe the dynamic CSF behavior from the CSF image.

In this case, in step S4, the display processing unit 44 performs display processing on the CSF image data and displays the CSF image data on the display device 34 after the display processing.

Figure 10:
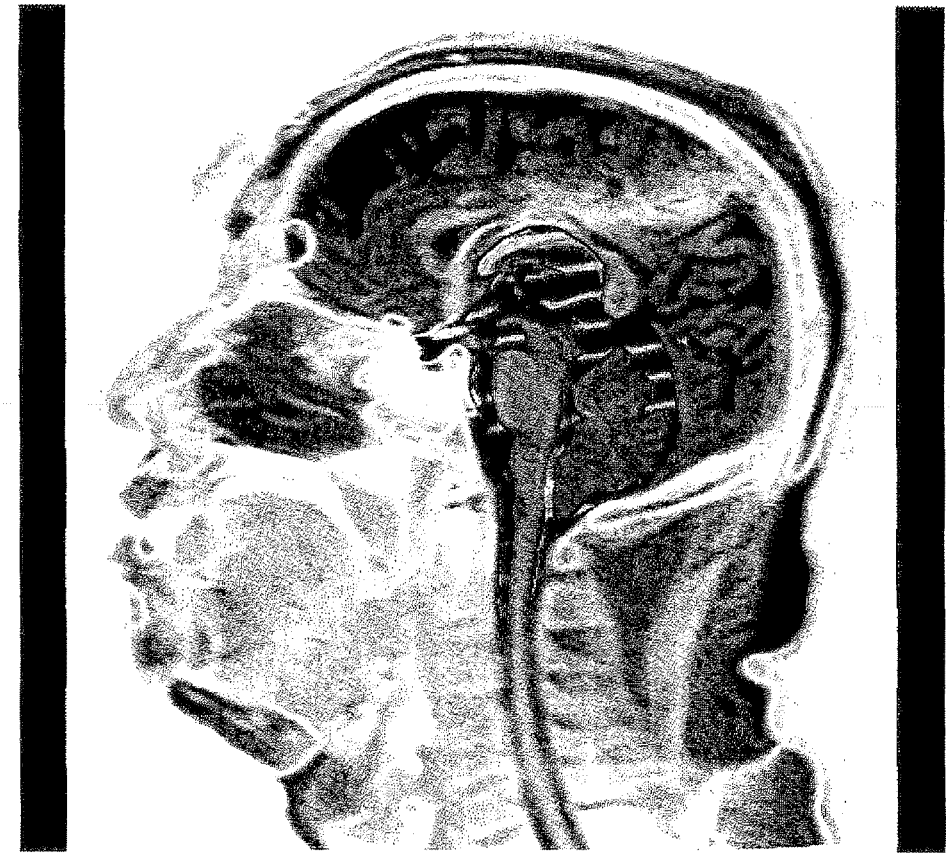
FIG. 10 is a chart showing an example of distinguishably displayed CSF obtained by performing display processing on the CSF image illustrated in FIG. 9.

FIG. 10 illustrates an example of a distinguishably (identifiably) displayed CSF obtained by performing display processing on the CSF image illustrated in FIG. 9. More specifically, signal inversion processing is performed on the data of the CSF image illustrated in FIG. 9 to invert the grayscale. Further, a signal threshold corresponding to the CSF region is set and coloring is performed on the CSF region extracted by the threshold processing. Then the CSF is distinguishably displayed more clearly. Note that the region having continuity in terms of signal intensity compared with the position extracted as the CSF region by the threshold processing may be re-extracted (expanded) as the CSF region with the use of a region growing algorithm, and then coloring may be performed on the re-extracted CSF region. The region growing algorithm is such that a determination is made as to whether a pixel located adjacent to the start point satisfies preliminarily specified conditions; if the conditions are satisfied, the adjacent pixel is determined to belong the same region; and this operation is repeated to extract the entire target region.

FIG. 10 illustrates the image in which CSF is made distinct by coloring the CSF region re-extracted by the region growing algorithm, in grayscale (achromatic color) for the sake of convenience.

In addition, it is possible to observe the flowing behavior of CSF as motion pictures like a cine image by displaying a plurality of CSF images each corresponding to a different data acquisition time in chronological order. Further, the detailed dynamic CSF behavior which is a portion to be observed can be easily understood by the color images. In this operation, it is desirable to display information on "which time phase of the respiration, heartbeat or body motion imaging time of each frame corresponds to" in parallel with each frame image, if acquisition of a respiratory gating signal or an ECG signal or monitoring of the body motion is performed in step S2.

Moreover, with the elapse of time from the imaging start time, the coloring criteria may be changed for each frame. As an example, consider the case where the SPAMM pulse is used as the labeling pulse and the region non-selective IR pulse is not applied before the labeling pulse (see FIG. 7C). Immediately after the labeling pulse as a saturation pulse is applied, the difference in longitudinal magnetization component Mz between the labeled CSF (whose longitudinal magnetization component Mz is close to zero) and the unlabeled CSF becomes large and the difference in NMR signal level therebetween also becomes large. As the time has elapsed since the labeling pulse was applied, the longitudinal magnetization component Mz of the labeled CSF also gradually recovers to the static magnetic field direction, and the difference in NMR signal level between the labeled CSF and the unlabeled CSF becomes small.

Here, assuming that white corresponds to 100% in grayscale representation and black corresponds to 0% in grayscale representation, the NMR signal from the unlabeled CSF is close to a highest signal level regardless of the data acquisition time and is displayed, for example, as a grayscale value of about 100% (white) in the CSF image. In contrast, the NMR signal from the labeled CSF is displayed, for example, as a grayscale value of about 0% (black) in a frame of an earliest data acquisition time, because its signal level is close to the lowest. However, the NMR signal from the labeled CSF is displayed, for example, as a grayscale value of about 50% (gray) in a frame of a late data acquisition time, because its signal level is increased by the recovery of the longitudinal magnetization component Mz.

Then, image processing is performed so that the labeled CSF is displayed commonly, for example, as yellow in all of the frames; and the unlabeled CSF is displayed commonly, for example, as red in all of the frames; and the extracted CSF region is displayed, for example, only in a color range from red to yellow. In this case, a grayscale value of 0% is displayed in yellow in the frame of the earliest data acquisition time; and the later the data acquisition time of one frame is, the higher percentage of grayscale value corresponding to yellow is allotted to the one frame. At the same time, a grayscale value of 100% is made to correspond to red regardless of the data acquisition time. The above image processing allows the labeled CSF to be displayed in the same chromatic color commonly in all of the frames, and thus the CSF behavior can be visually distinguished in an easy manner.

Figure 11:
FIG. 11 is a chart showing another example of distinguishably displayed CSF obtained by performing display processing on the CSF image imaged by setting the labeling region to a stripe pattern.

FIG. 11 illustrates another example of a distinguishably displayed CSF obtained by performing display processing on the CSF image data imaged by setting the labeling region to a stripe pattern.

Figure 12:
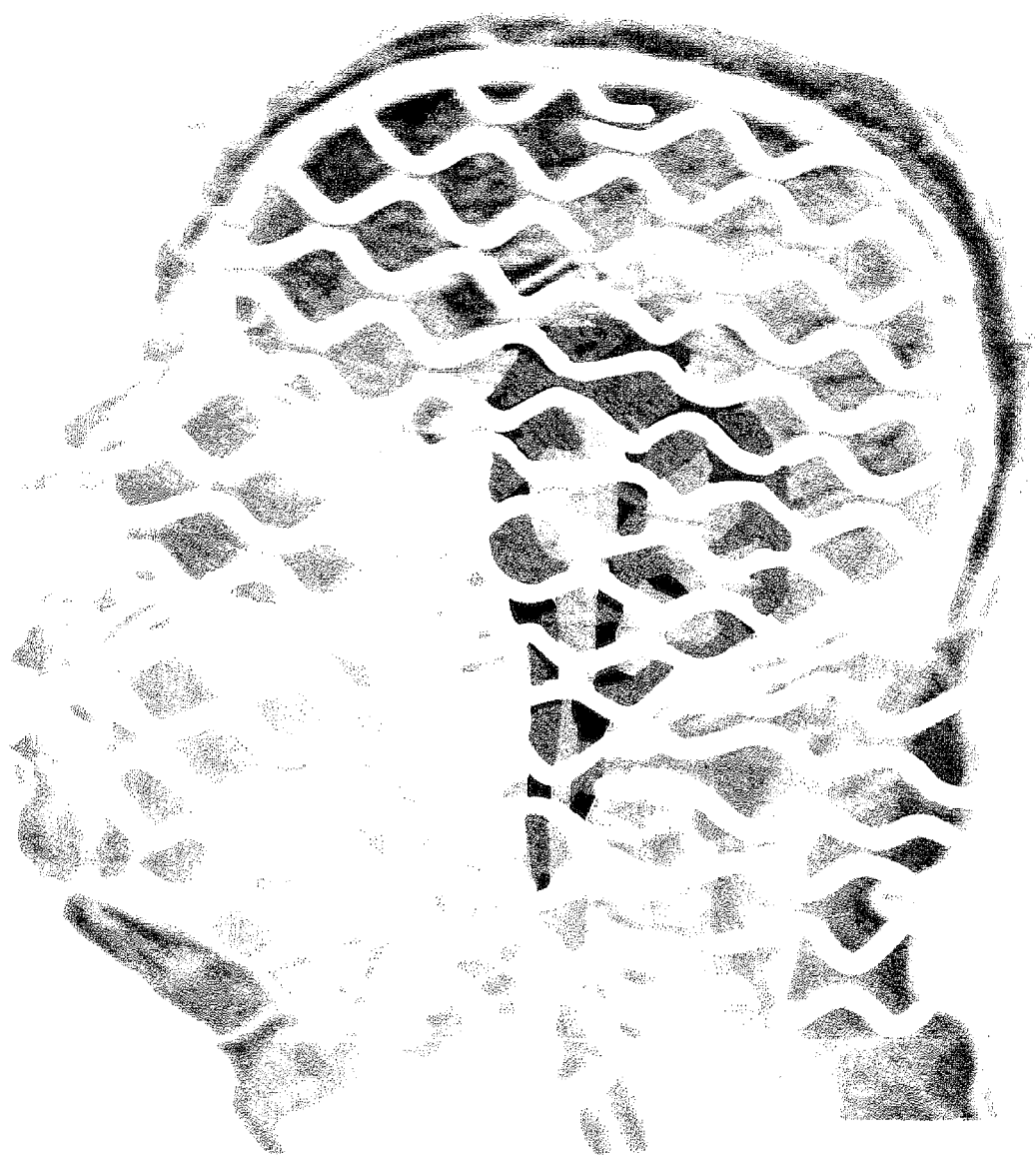
FIG. 12 is a chart showing an example of a distinguishably displayed CSF obtained by performing display processing on the CSF image imaged by setting the labeling region to a grid pattern.

FIG. 12 illustrates an example of a distinguishably displayed CSF obtained by performing display processing on the CSF image data imaged by setting the labeling region to a grid pattern.

Figure 13:
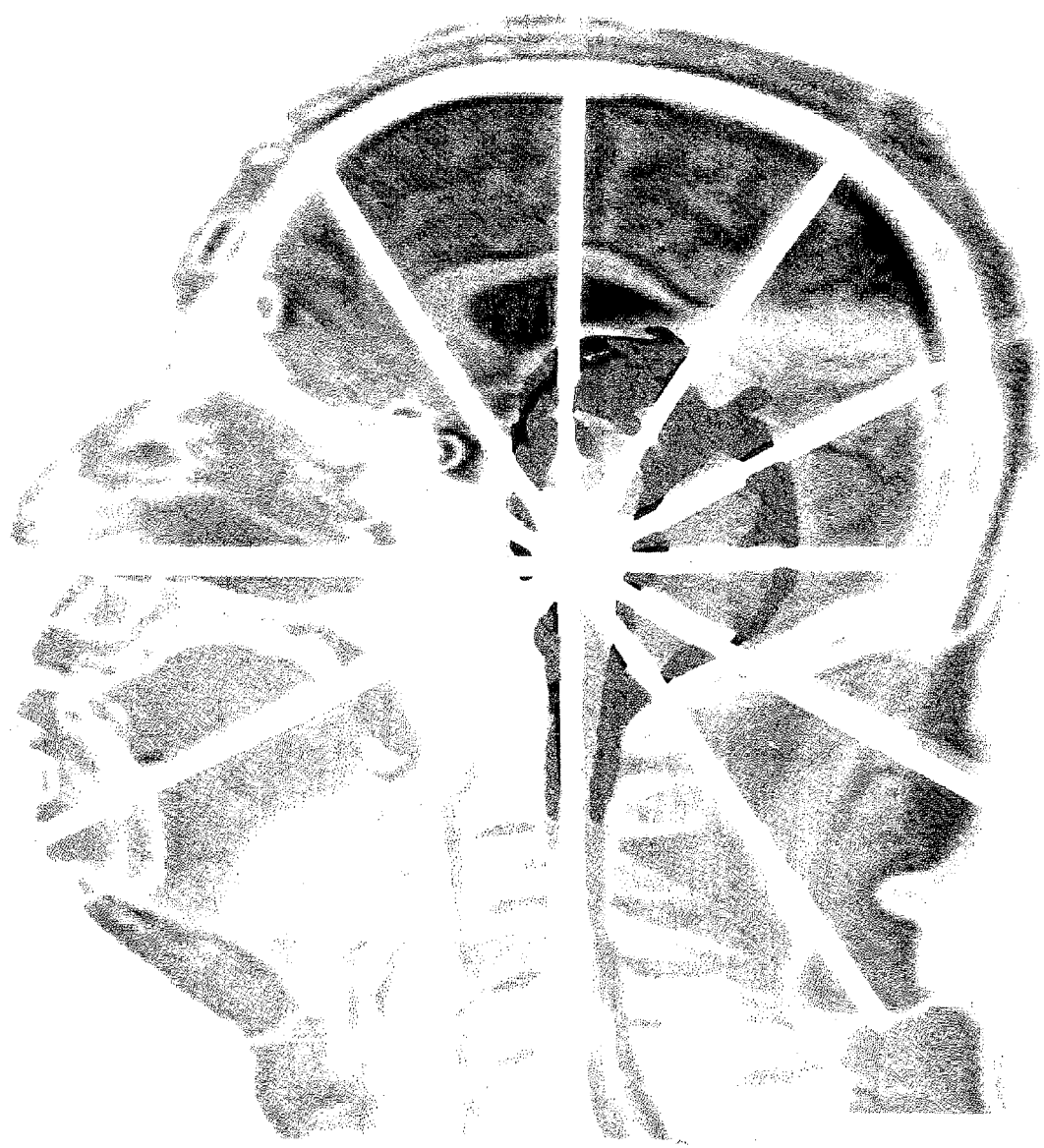
FIG. 13 is a chart showing an example of a distinguishably displayed CSF obtained by performing display processing on the CSF image imaged by setting the labeling region to a radial pattern.

FIG. 13 illustrates an example of a distinguishably displayed CSF obtained by performing display processing on the CSF image data imaged by setting the labeling region to a radial pattern.

In FIGS. 11, 12 and 13, the CSF image is displayed in black and white grayscale. However, in fact, in FIGS. 11, 12 and 13, the completely black regions are displayed in yellow as the labeled CSF, and the gray regions are displayed in red as the unlabeled CSF.

As illustrated in FIGS. 11, 12 and 13, it can be confirmed that patterns each labeled as a stripe, grid or radial shape are formed through the entire image. The labeled CSF displayed in yellow is out of the labeling pattern region labeled as the stripe, grid or radial shape. From the above fact, it can be confirmed that the CSF is moving.

Figure 14:
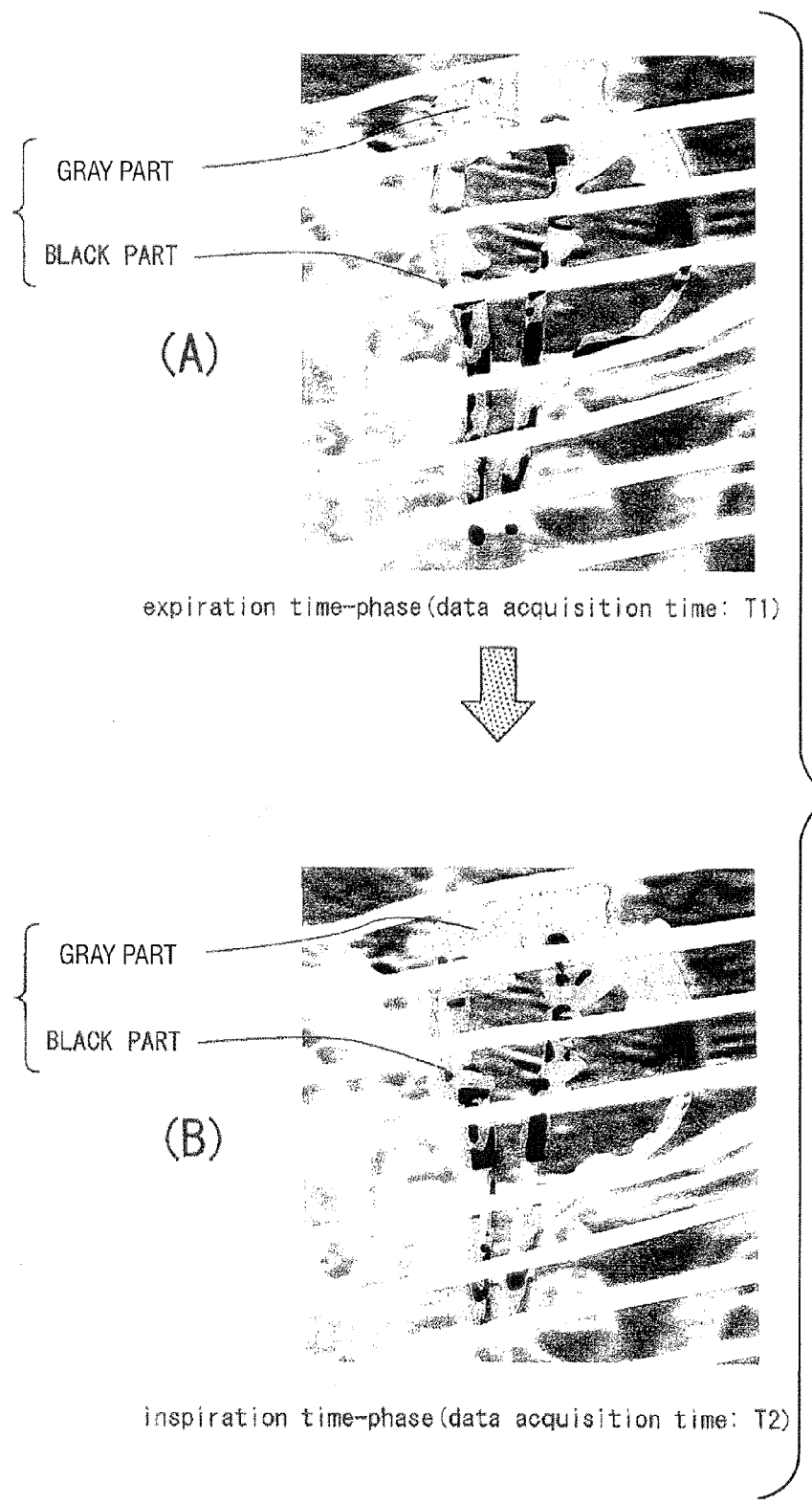
FIG. 14 is a chart showing a plurality of CSF images, each corresponding to a different time, displayed in chronological order, when imaging is performed by acquiring the respiratory gating signal.

FIG. 14 illustrates another example of a distinguishably (identifiably) displayed CSF obtained by performing the same display processing as in FIG. 11 on the CSF image data imaged by setting the labeling region to a stripe pattern. FIG. 14 enlarges the CSF portion in the head (center portion of the image in FIG. 11). FIG. 14 displays a plurality of CSF images each corresponding to a different time in chronological order (as FIGS. 14A and 14B), when imaging is performed by acquiring the respiratory gating signal in step S2. FIG. 14A corresponds to the image obtained at a data acquisition timing (imaging time) T1, and corresponds to the exhalation time phase. FIG. 14B corresponds to the image obtained at a data acquisition timing (imaging time) T2, and corresponds to the inhalation time phase. In this example, T2 is later than T1 in terms of time.

FIG. 15 illustrates an example of a plurality of CSF images each corresponding to a different imaging time displayed in chronological order in the same manner as in FIG. 14, when monitoring is performed on the abdominal motion in step S2. FIG. 15A corresponds to the image obtained at a data acquisition timing (imaging time) T3, and corresponds to the exhalation time phase. FIG. 15B corresponds to the image obtained at a data acquisition timing (imaging time) T4, and corresponds to the inhalation time phase. In this example, T4 is later than T3 in terms of time.

Although the CSF image is displayed in grayscale in FIGS. 14 and 15, in fact, the completely black regions ('black parts' as shown in FIGS. 14 and 15) are displayed in yellow as the labeled CSF, and the gray regions ('gray parts' as shown in FIGS. 14 and 15) are displayed in red as the unlabeled CSF in FIGS. 14 and 15.

As illustrated in FIGS. 14 and 15, it is desirable to display information on "which respiration time phase imaging time of each frame corresponds to" under each frame image.

In FIG. 14A, the CSF flow rate can be calculated by detecting how far the CSF of specific portion labeled by a pattern such as a stripe moves in the CSF image in the frame of FIG. 14B and by dividing the moving distance by the time difference (T2−T1) in imaging time between the two frames. In FIG. 15, the CSF flow rate can be calculated in the same manner.

(Advantages)

As described above, the magnetic resonance imaging apparatus 20 according to the present invention applies a labeling pulse (after a region non-selective IR pulse is applied or without applying the region non-selective IR pulse), consecutively acquires CSF image data of a plurality of frames, each corresponding to a different imaging (data acquisition) time, performs display processing such as coloring on the CSF image data, and distinguishably displays the CSF. More specifically, labeling is performed once, and then data acquisition corresponding to each frame of CSF image is consecutively (continuously) performed. Consequently, the labeled CSF is the same for each frame. Therefore, CSF image data allowing the dynamic CSF behavior to be easily understood can be acquired. Moreover, a wide range of dynamic CSF behavior can be continuously depicted.

Clinically expressed, when the CSF is not moving, its state of being stopped can be surely determined. In the case of a normal CSF, it is possible to visualize how the CSF moves. For example, hydrocephalus and subarachnoid hemorrhage indicate that the CSF does not move and may have similar symptoms, but are different in the portion where the CSF does not move. Therefore, according to the magnetic resonance imaging apparatus 20, hydrocephalus and subarachnoid hemorrhage can be distinguished.

In addition, according to the magnetic resonance imaging apparatus 20, the dynamic CSF behavior can be understood, and thus the CSF flow rate can be measured. Specifically, the CSF flow rate can be calculated by detecting how far the CSF of specific portion labeled by a pattern such as a stripe moves in the CSF image in the next frame and by dividing the moving distance by the time difference in imaging (data acquisition) time between the two frames.

Further, unlike the conventional t-SLIP method, a plurality of BBTIs need not be set, and thus image data without a time difference can be acquired.

Note that the magnetic resonance imaging apparatus 20 allows any fluids such as blood other than the CSF to be imaged in the same manner. In particular, the magnetic resonance imaging apparatus 20 is suitable for imaging non-periodic fluids.

What is claimed is:

1. A magnetic resonance imaging (MRI) apparatus comprising:
a magnetic resonance (MR) data acquisition unit which consecutively acquires a plurality of MR data sets from a region of interest, each acquired MR data set corresponding to a different data acquisition time, after a labeling pulse is applied to a region of interest without applying any labeling pulse between the consecutive data acquisitions and without substantial time delay between the consecutive data acquisitions; and
a cerebrospinal fluid (CSF) image data generation unit which generates a plurality of CSF image data sets based on the plurality of MR data sets, wherein each CSF image data set corresponds to a respective one of the MR data sets.

2. The MRI apparatus according to claim 1, wherein the MR data acquisition unit is configured to apply a saturation pulse as the labeling pulse.

3. The MRI apparatus according to claim 2, wherein the MR data acquisition unit is configured to apply a region non-selective inversion recovery pulse before the labeling pulse is applied.

4. The MRI apparatus according to claim 3, wherein the CSF image data generation unit is configured to generate the plurality of CSF image data sets using REAL reconstruction processing.

5. The MRI apparatus according to claim 1, further comprising:
a display processing unit which performs display processing to distinguishably display a CSF region in the plurality of CSF image data sets.

6. The MRI apparatus according to claim 1, further comprising:
a monitoring unit which monitors a periodic body motion of an object in a period while the plurality of MR data sets are being consecutively acquired; and
a display processing unit which generates and displays a plurality of CSF images based on the plurality of CSF image data sets, and displays information on timing of the body motion with respect to the acquisition time of MR data sets for each of the plurality of CSF images, based on monitoring results of the monitoring unit.

7. The MRI imaging apparatus according to claim 1, wherein
the MR data acquisition unit is configured to apply a time spatial labeling inversion pulse as the labeling pulse.

8. The MRI imaging apparatus according to claim 1, wherein
the MR data acquisition unit is configured to apply a SPAMM (spatial modulation of magnetization) pulse or DANTE (delays alternating with nutations for tailored excitation) pulse as the labeling pulse.

9. The MRI imaging apparatus according to claim 1, wherein
the MR data acquisition unit is configured to selectively apply the labeling pulse to a stripe patterned region or a grid patterned region of the CSF to be imaged.

10. The MRI imaging apparatus according to claim 1, wherein
said MR data acquisition unit is configured to selectively apply the labeling pulse to a radial patterned region of the CSF to be imaged.

11. The MRI apparatus according to claim 1, further comprising:
a calculation unit which
extracts each of plural regions of CSF by performing threshold processing on each of the plurality of CSF image data sets;
then detects a moving distance of the CSF labeled between the plurality of CSF image data sets; and
calculates a flow rate of the CSF based on the moving distance and interval of acquisition times of the plurality of MR data sets corresponding to said image data sets.

12. The MRI apparatus according to claim 1, wherein the MR data acquisition unit is configured to simultaneously apply the labeling pulse to a plurality of regions.

13. A magnetic resonance imaging (MRI) apparatus comprising:
- a magnetic resonance (MR) data acquisition unit which consecutively acquires a plurality of MR data, each corresponding to a different data acquisition time, after a labeling pulse is applied to a region of interest; and
- a cerebrospinal fluid (CSF) image data generation unit which generates a plurality of CSF image data based on the plurality of MR data so as to correspond to each of the plurality of MR data;
- a calculation unit which extracts each of regions of CSF by performing threshold processing on each of the plurality of CSF image data;
- then detects a moving distance of the CSF labeled between the plurality of CSF image data; and
- calculates a flow rate of the CSF based on the moving distance and interval of acquisition times of the plurality of MR data.

14. A magnetic resonance imaging (MRI) method comprising:
- applying a magnetic resonance (MR) labeling pulse to a region of interest;
- consequently acquiring a plurality of MR data sets from said region of interest, each acquired MR data set corresponding to a different data acquisition time, after the labeling pulse is applied to said region of interest without applying any labeling pulse between the consecutive data acquisitions and without substantial time delay between the consecutive data acquisitions; and
- generating a plurality of cerebrospinal fluid (CSF) image data sets based on respectively corresponding ones of the plurality of MR data sets.

* * * * *